United States Patent [19]
Lund

[11] 4,245,052
[45] Jan. 13, 1981

[54] DISPOSABLE MICROBIAL PROFILE TRAY

[75] Inventor: Marlys E. Lund, Eden Prairie, Minn.

[73] Assignee: Minnesota Mining and Manufacturing Company, St. Paul, Minn.

[21] Appl. No.: 53,437

[22] Filed: Jun. 29, 1979

[51] Int. Cl.² .............................................. C12M 1/20
[52] U.S. Cl. .................. 435/301; 356/246; 422/102; 435/808
[58] Field of Search ................ 422/102; 356/246; 435/301, 299, 300, 808

[56] References Cited

U.S. PATENT DOCUMENTS

| | | | |
|---|---|---|---|
| 3,107,204 | 10/1963 | Brown et al. | 435/33 |
| 3,356,462 | 12/1967 | Cooke et al. | 422/102 |
| 3,785,928 | 1/1974 | Kessler | 435/287 |
| 4,099,881 | 7/1978 | Vanden Broek et al. | 356/244 X |
| 4,154,795 | 5/1979 | Thorne | 422/99 |

FOREIGN PATENT DOCUMENTS 170898  9/1951  Austria .

Primary Examiner—Robert J. Warden
Attorney, Agent, or Firm—Cruzan Alexander; Donald M. Sell; John C. Barnes

[57] ABSTRACT

A microbial profile tray formed of a light transmitting material and having a planar surface in which a plurality of uniformly shaped cup-like receptacles have their openings. Some of these cup-like receptacles have a surface which causes transmitted light to be diffused. The cup-like receptacles having the light diffusing surface can be used as control cups to simulate the turbidity which occurs in cups not having this light diffusing surface but in which microbial growth has occurred.

6 Claims, 3 Drawing Figures

DISPOSABLE MICROBIAL PROFILE TRAY

FIELD OF THE INVENTION

This invention relates to a titration tray having a plurality of receptacles containing various biochemical test media in which microorganisms can be incubated and identified.

The initial receptacles in which these tests were performed were test tubes or disc-plates, however the multiple handlings of these independent receptacles were too expensive and time-consuming, thus titration trays were developed. These trays were generally molded plastic trays with a large number of small open cups serving as individual "test tubes" integral with a tray (see e.g. U.S. Pat. No. 3,356,462). These trays eliminated the handling of many independent receptacles and constituted a vehicle in which a plurality of test cultures were contained in a separated, but closely spaced condition so that comparative colorimetric determinations could be made. When these colorimetric determinations are made, a technician is comparing a cup that has a color change resulting from a microbial growth reacting with the biochemical, with an adjacent cup in which no growth has occured. The microbial growth also causes a turbid condition in the cups as light which is transmitted through the cups is scattered by the microbial particles. When a drastic color change occurs, the light scattering has virtually no effect on the color comparison. However for a very subtle color change, the light scattering interferes with the color interpretation and greatly increases the chance of error during this identification process.

SUMMARY OF THE INVENTION

The present invention provides a mircobial profile tray which has control cup-like receptacles which simulate the turbility caused by the growth of microorganisms and thus diminishes the chance of error.

The tray is formed from a polymeric or similar transparent material and has a planar surface in which a plurality of uniformly shaped cup-like receptacles have their openings. Some of these cup-like receptacles have a lower end part the surface of which causes transmitted light to be diffused. The cup-like receptacles having this light diffusing surface can be used as control cups to simulate the turbidity which occurs in cups not having this light diffusing surface but in which microbial growth has occured. With this structure, the present invention isolates the resultant color change from the concomitant turbidity.

DESCRIPTION OF THE ACCOMPANYING DRAWINGS

The present invention will be further described hereinafter with reference to the accompanying drawing wherein.

DETAILED DESCRIPTION OF THE PREFERRED EMBODIMENT

Figure 1:
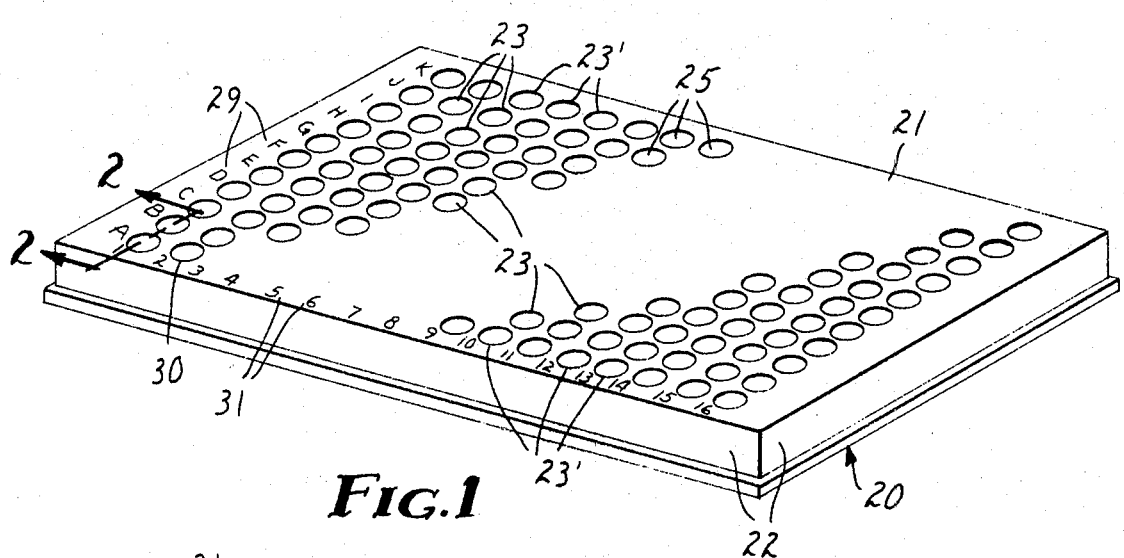
FIG. 1 is a perspective view of a microbial profile tray according to the present invention.
Figure 2:
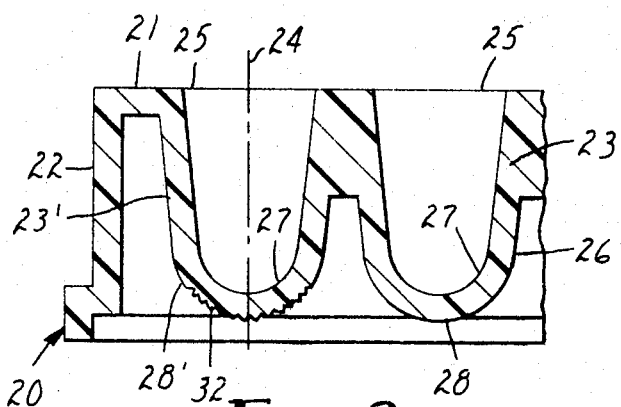
FIG. 2 is an enlarged fragmentary verticle sectional view taken along the line 2—2 of FIG. 1.

Referring now to the drawings, the microbial profile tray 20 according to the present invention is injection molded of a polymeric material such as polystyrene or any other suitable material having the required properties of transparency, strength, and impermeability. The tray 20 is generally rectangular in shape and has a planar top surface 21 and perpendicular side walls 22. A plurality of cup-like receptacles 23 have their openings 25 integral with this planar top surface 21. These cup-like receptacles 23 extend generally downward from the planar top surface 21 and have a longitudinal axis 24 which is perpendicular to the planar top surface 21. The cup-like receptacles 23 have lower end parts 26 which are hemispherical in shape, and which have an inner surface 27 and an outer surface 28. This outer surface 28 is smooth such that parallel light rays will continue to be generally parallel even after passing through this surface. As can be seen in FIG. 1, the cup-like receptacles are arranged in an array which has rows labeled alphabetically 29 and columns labeled numerically 31. Thus, each cup-like receptacle can be identified by a letter-number combination, e.g., cup A2 (30).

Figure 3:
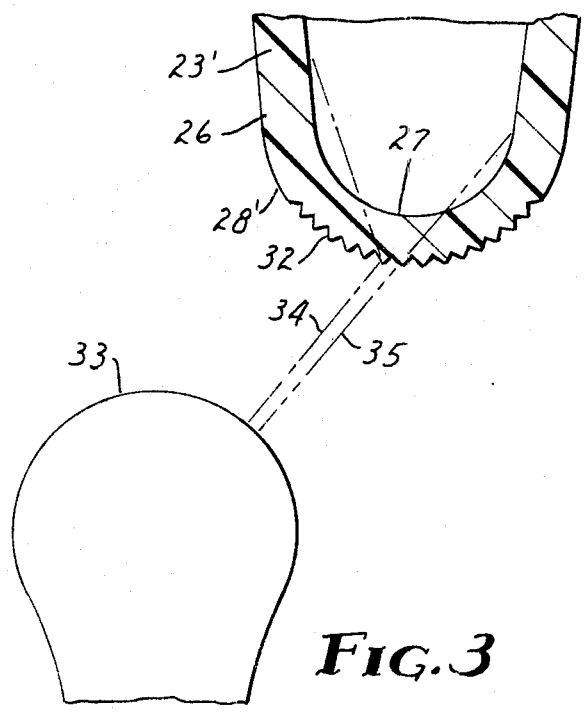
FIG. 3 is an enlarged fragmentary view of the tray in FIG. 1, illustrating the effect of a light diffusing surface of the tray on transmitted light.

Certain of the cup-like receptacles 23 have been modified to contain a light diffusing surface 32. These modified cup-like receptacles or control cups are designated 23' and are located in rows A and K of the tray 20. This light diffusing surface 32 can be sandblasted, etched, or coated on the cup-like receptacles 23, or the mold (not shown) in which the tray 20 is made can contain roughened surfaces resulting in similar roughened surfaces on the cups. For optimum use the methods should result in an irregular profile containing surfaces with dimensions in the range of ½ to 1 micrometer. This range results in surfaces within the irregular profile which simulate the dimensions of the particles causing the light scattering in the case of microbial growth. This is illustrated in FIG. 3 where some of the rays of light transmitted from lamp 33 are able to pass through the light diffusing surface 32 undeflected (35), while other rays (34) are deflected by the surface. Although the light diffusing surface 32 is shown on the outer surface 28' of the cup-like receptacles 23', it could be placed on the inner surface 27 and still provide the desired effect.

The preferred embodiment of the microbial profile tray 20 has a length of 17.5 centimeters and a width of 11 centimeters. The cup-like receptacles 23 within a given row are spaced 10 millimeters apart while the spacing between rows (i.e., between cup-like receptacles within a column) are spaced 9 millimeters apart. Each cup-like receptacle 23 has a depth of 10 millimeters, a diameter of 7 millimeters at the opening, and a radius of curvature of 3 millimeters on the hemispherical lower end part 26. Although this embodiment is preferred other configurations as to tray shape, cup shape, and number of cups can be comtemplated.

In operation, the receptacles in rows C through I contain various antibiotics in which certain laboratory tests will be performed. Rows A, B, J & K contain different biochemicals in matched pairs such that the chemical in A3 is essentially the same as that in B3, and likewise the chemical in J6 is essentially the same as that in K6. In a given column of cup-like receptacles the only structural difference between rows A & B is the presence of the light diffusing surface 32 on the cuplike receptacle 23' of row A. This concept is also true for rows J and K wherein the cup-like receptacle 23' of row K have the light diffusing surface 32. Microorganisms are incubated in the cup-like receptacles 23 of rows B through J. If a microbial growth occurs, light passing through the lower end parts 26, and through the cup-like receptacles 23 will be deflected by the microbial growth and cause a turbid condition within the cup 23. If the microbial growth has also reacted with the biochemical, a color change will occur. The cup-like receptacles 23' of rows A and K are not inoculated with microorganisms and no microbial growth occurs, hence no color change occurs. The turbidity however of microbial growth is simulated by the light diffusing surface 32 which deflects light as it passes through the irregular profile. A comparison can be made of a particular cup-like receptacle 23 in row B with its counterpart in row A. If microbial growth has occured, both A and B will appear to have a turbid condition, however, only the cup-like portion 23 of row B will have a color change.

Having thus described a preferred embodiment of the present invention it will be understood that changes may be made in size, shape, or configuration of some of the parts without departing from the present invention as described in the appended claims.

What is claimed is:

1. A microbial profile tray formed of a light-transmitting material and comprising a plurality of uniformly shaped cup-like receptacles having their openings integral with a planar surface, said cup-like receptacles having a lower end part, wherein some of said lower end parts have a surface finish which is smooth such that parallel light rays transmitted through said surfaces will continue to be generally parallel, and wherein some of said lower end parts have a light diffusing surface finish such that transmitted light will be diffused, and such that the diffusion due to said light diffusing surface finish will simulate the light diffusion which occurs when light is transmitted through a solution in which microbial growth has occured.

2. A microbial profile tray as claimed in claim 1 wherein said light diffusing surface finish of said lower end part is on the outer surface of said lower end part.

3. A microbial profile tray as claimed in claim 1 or 2 wherein said light diffusing surface finish comprises a roughened surface having an irregular profile through which transmitted light will be diffused.

4. A microbial profile tray as claimed in claim 3 wherein said array comprises matched pairs of smooth surfaced lower end parts and rough surfaced lower end parts such that microbes grown in said cup-like receptacles having smooth surfaced lower end parts will cause the diffusion of light being transmitted through said cup-like receptacle and the microbial growth therein, and such that said cup-like receptacles having rough surfaced lower end parts will cause the diffusion of light being transmitted through their irregular profile, thereby allowing comparison between said two different cup-like receptacles with light diffusion not being a variable.

5. A microbial profile tray as claimed in claim 1 wherein said cup-like receptacles are arranged in a rectangular array so as to afford identification of each cup-like receptacle.

6. A microbial profile tray as claimed in claim 5 wherein said array comprises matched pairs of smooth surfaced lower end parts and rough surfaced lower end parts such that microbes grown in said cup-like receptacles having smooth surfaced lower end parts will cause the diffusion of light being transmitted through said cup-like receptacle and the microbial growth therein, and such that said cup-like receptacles having rough surfaced lower end parts will cause the diffusion of light being transmitted through their irregular profile, thereby allowing comparison between said two different cup-like receptacles with light diffusion not being a variable.

* * * * *